United States Patent [19]

Cheo

[11] 4,197,457
[45] Apr. 8, 1980

[54] SYSTEM FOR DETECTING FOREIGN PARTICLES OR VOIDS IN PLASTIC MATERIAL AND METHOD

[75] Inventor: Peter K. Cheo, West Hartford, Conn.

[73] Assignee: Electric Power Research Institute, Inc., Palo Alto, Calif.

[21] Appl. No.: 909,255

[22] Filed: May 24, 1978

[51] Int. Cl.² ............................................. G01J 1/00
[52] U.S. Cl. ................................... 250/339; 250/341
[58] Field of Search ........... 250/339, 340, 341, 358 R, 250/359, 360, 562, 563, 572

[56] References Cited

U.S. PATENT DOCUMENTS

| 3,405,270 | 10/1968 | Briggs | 250/341 |
| 3,693,025 | 9/1972 | Brunton | 250/339 X |
| 3,825,755 | 7/1974 | Ruskin | 250/339 |
| 3,870,884 | 3/1975 | Williams | 250/339 |
| 4,085,326 | 4/1978 | Williams | 250/339 |

Primary Examiner—Davis L. Willis
Attorney, Agent, or Firm—Flehr, Hohbach, Test

[57] ABSTRACT

A system for detecting foreign particles or voids in plastic material is disclosed herein and utilizes a far-infrared laser beam of electromagnetic radiation at a given wavelength. This laser beam is directed into the plastic material such that any portion thereof passing through the material unobstructed by voids or foreign matter does so along a predictable primary beam path, and such that any portion impinging a void or foreign particle is caused to scatter along predictable scattering paths including paths which are different than the primary beam path. In this way, at least one detector can be properly aligned in at least one of these different scattering paths for detecting a portion of the scattered radiation, thereby indicating the presence of a void or foreign particle.

15 Claims, 4 Drawing Figures

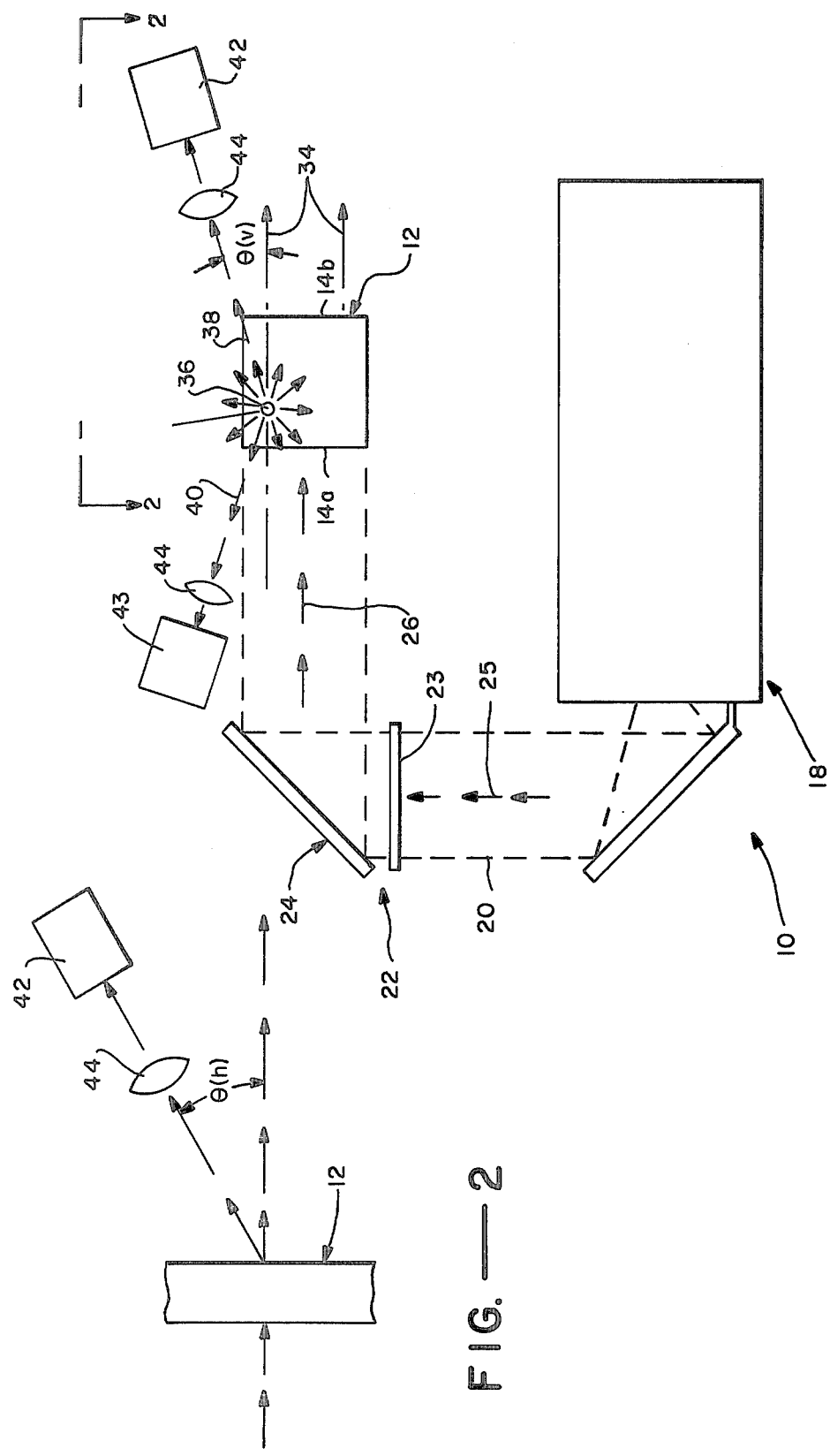

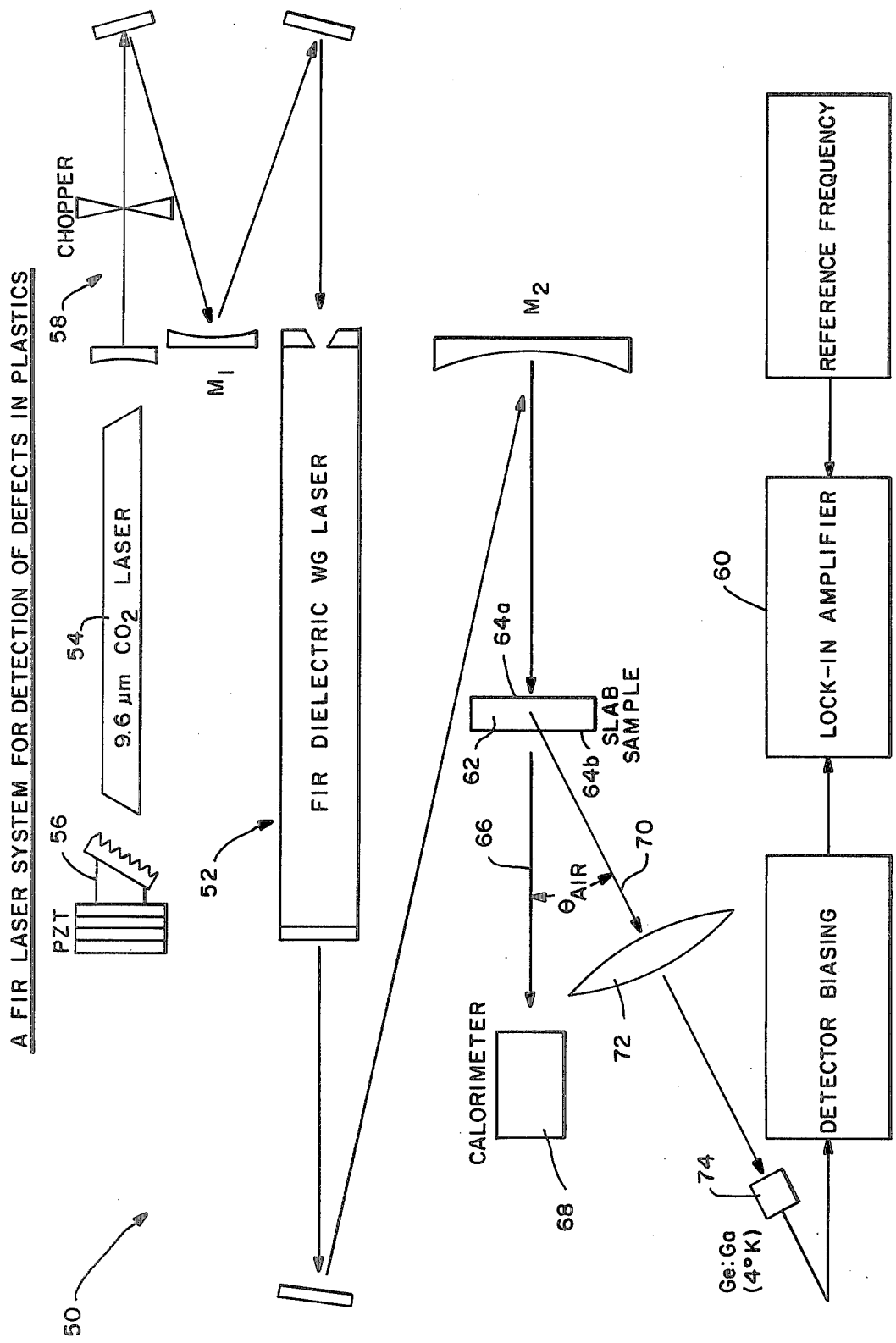
FIG.—3

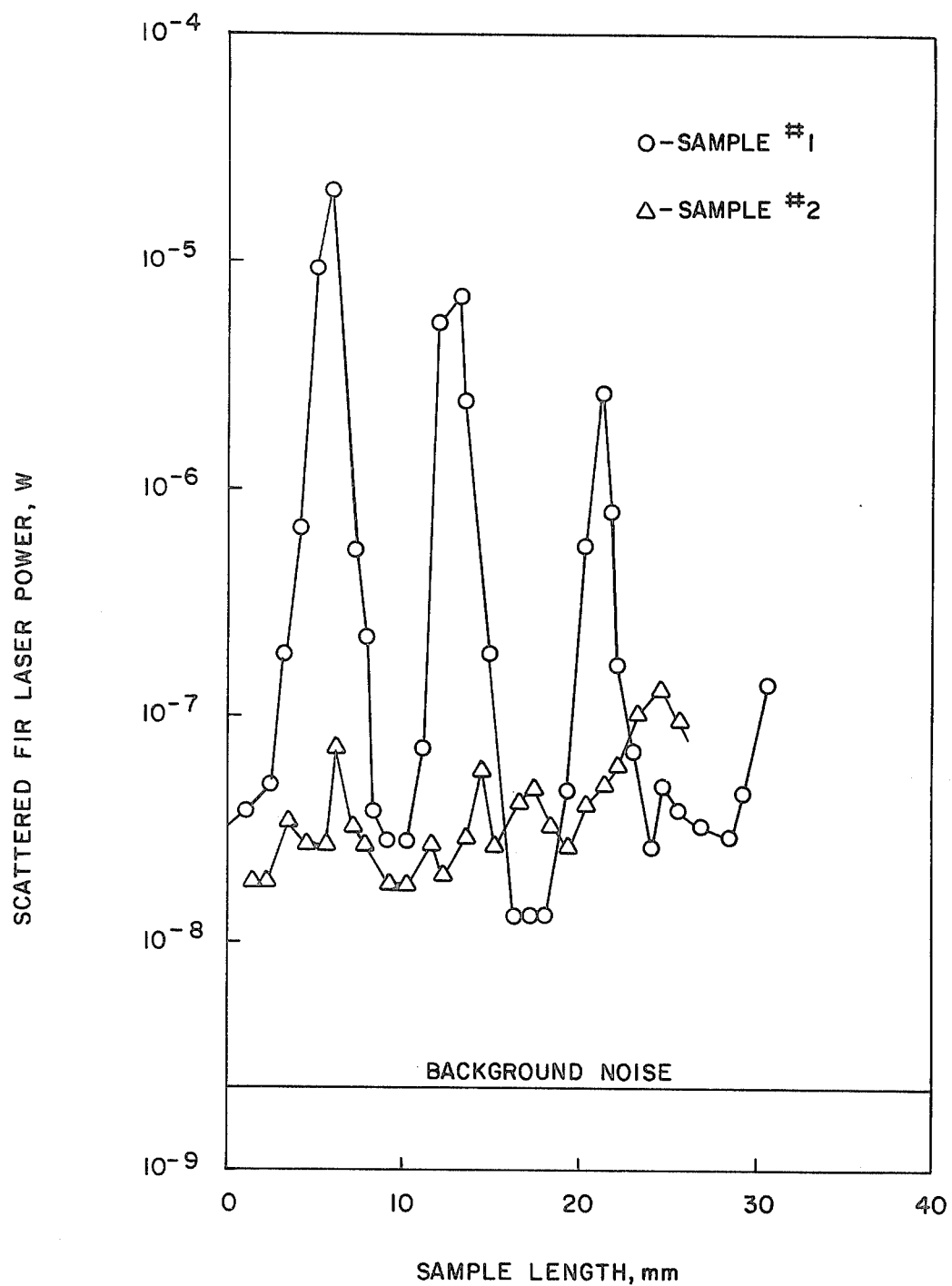
FIG.—4

SYSTEM FOR DETECTING FOREIGN PARTICLES OR VOIDS IN PLASTIC MATERIAL AND METHOD

BACKGROUND OF THE INVENTION

The present invention relates generally to a system for detecting foreign particles or voids in plastic material, and more particularly to a method and technique for remote and nondestructive detection of defects such as voids, contaminants, and flaws etc., inside nonconducting thermoplastic materials, such as polyethylene, PVC, or any far-infrared transparent media. The disclosed detection scheme for defects in plastics utilizes a far-infrared (FIR) laser emitting in the submillimeter wave region at which most plastic materials become transparent as if the visible light passes through glass. Either a single or a cluster of defects inside a solid dielectric medium will scatter the laser beam in a predictable manner in predominantly either the forward or the backward direction depending on the nature of the defects. The captured scattered radiation pattern can be related to the size, shape, and the type of defects. This disclosure provides the basic method and technique for flaw detection in solid dielectrics, which are opaque to the light in the visible and the near infrared ($\lambda < 70$ microns) region.

X-rays and ultrasonic waves have been often used to image and to detect defects and structural characteristics of opaque materials. For a class of materials such as plastics, these methods are not suitable. X-rays methods do not provide sufficient contrast ratio between the defects such as voids and micro-cracks and the medium in order to establish a clear image. Ultrasonic waves on the other hand can not propagate very deeply into plastic materials because of excessive loss of the media at the acoustic frequencies.

Plastic materials are increasingly used in the present-day consumer and industrial products. There is a need for a reliable, nondestructive method to inspect and to characterize the quality of these products. Because of inadequate quality control, plstic materials have not been widely used by the automotive, marine and building industries. This invention discloses a method by which the defects as small as a few microns in size can be reliably detected inside an opaque plastic material without destroying the object. This method utilizes a far-infrared laser scattering process by which the scattered light as a result of a small localized difference in the refractive index inside the plastic medium produces a characteristic pattern and is completely deviated from the primary laser beam in the forward direction. From the measurements of the scattered light, it has been demonstrated that the character of the defects can be recognized.

Laser scattering techniques have been used frequently to determine, for example, the surface (Ref. 1, P. K. Cheo and J. Renau, J. Opt. Soc. Am. 59, 821, 1969) the aerosol (Ref. 2, F. B. Fernald, et al., Opt. Quant. Elect. 7, 141, 1975) and others. However, these techniques are different from this disclosure, in that, they utilize only the reflection or so-called back-scattering of light. In these cases, the optical absorptivity of the medium is not crucial to the applicability of these detection methods. To detect small defects in plastic materials, it is necessary to select laser wavelengths such that not only the laser can penetrate the medium but also can provide adequate resolution to recognize the character of the defects. In other words, the method disclosed herein requires specific laser wavelengths which fall in the range from 70 microns to 2000 microns.

The absorption coefficient of most plastics such as polyethylene, polypropylene, teflon, etc., decreases montonically with increasing laser wavelength. On the other hand, the scattered laser power, in general, decreases with increasing wavelength for the size of defects in the proximity of one optical wavelength. For these reasons the choice of laser wavelength is an important consideration for the design of a detection system which is required to detect defects having a specific size range of interest.

OBJECTS AND SUMMARY OF THE INVENTION

In view of the foregoing, one object of the present invention is to provide a particular system for detecting foreign particles, specifically very small contaminants or voids in plastic material.

Another object of the present invention is to provide a system which is relatively uncomplicated in design and reliable in use.

Still another object of the present invention is to provide a system which utilizes a far-infrared laser scattering technique for detecting the voids and contaminants within the plastic material and particularly a system which reliably distinguishes between scattered radiation (from the voids or contaminants) and background radiation (including non-scattered radiation which passes through the plastic material.

A further object of the present invention is to provide a method of detecting foreign particles or voids in plastic material utilizing a system of the type described.

As will be discussed in detail hereinafter, the system (or method) disclosed herein utilizes a far-infrared laser beam of electromagnetic radiation which has a wavelength compatible with the absorption coefficient of the plastic material being monitored for allowing the beam to pass therethrough. This beam of far-infared radiation is directed into the plastic material along a path incident to and at a predetermined orientation with the plastic material (1) such that any portion of the beam which passes through the material unobstructed by voids or foreign matter within the latter does so along predictable paths and (2) such that any portion which impinges a void or foreign particle is scattered thereby along predictable scattering paths including paths different than the unobstructed paths. In this way, at least one device for detecting electromagnetic radiation at the same wavelength can be positioned in alignment with at least one of the different scattering paths for detecting the scattered radiation along that path for indicating the presence (or absence) of a void or foreign particle.

The specific details of this system (or method) will be discussed hereinafter. For the moment, it suffices to say that it utilizes a well controlled beam of electromagnetic radiation and a carefully positioned detector for discriminating between the presence or absence of an internal void or foreign particle in an uncomplicated and yet reliable way. This simple method for detection of defects such as voids, micro-cracks, and contaminants inside plastic materials (preferably those opaque to visible light) will be disclosed hereinafter, as just stated. This method affords a nondestructive inspection and quality control of plastic materials which is opaque to the visible light.

BRIEF DESCRIPTION OF THE DRAWINGS

FIG. 1 is a diagrammatic illustration of a system which is constructed in accordance with the present invention and which is provided for detecting foreign particles or voids in specific plastic material.

FIG. 2 is a diagrammatic illustration of a portion of the system illustrated in FIG. 1, taken generally along line 2—2 of FIG. 1.

FIG. 3 is a diagrammatic illustration of a second system which is also constructed in accordance with the present invention and which is provided for the detection of defects such as foreign particles or voids inside plastic materials.

FIG. 4 shows the measurements obtained by using the system illustrated in FIG. 3, each peak in these measured curves representing a well defined defect size inside the plastics, the background noise representing the level of the detector noise when the far-infrared laser beam comprising part of the system is turned off and the valleys in these curves representing the minimal scattering background from plastics which contain a high density of microvoids ($10^9$/c.c.).

DETAILED DESCRIPTION AND PREFERRED EMBODIMENTS

Turning now to the drawings, wherein like components are designated by like reference numerals throughout the various figures, attention is specifically directed to FIG. 1 which illustrates a system 10 constructed in accordance with the present invention and generally designated by the reference numeral 10. As stated previously, this system is provided for detecting foreign particles or voids in plastic material which is generally indicated at 12, specifically nonconducting thermoplastic materials such as polyethylene, polyvinylchloride, or any far-infrared transparent media. This material, in a preferred embodiment, has a known index of refraction and an absorption coefficient sufficient to pass electromagnetic radiation of a given wavelength, specifically a wavelength from 70 microns to 2000 microns and has substantially flat front and back sides 14a and 14b. As will be seen, the foreign particles and voids which can be detected are of sizes within a range depending upon the wavelength selected or stated conversely, the wavelength is selected depending upon the size of defect to be detected. In one actual working embodiment of the present invention, plastic material 12 is conventional cross-linked polyethylene extruded insulation which displays an index of refraction of approximately 1.5 and an absorption coefficient less than ($<$)1 cm$^{-1}$ when a laser beam of far-infrared radiation having a wavelength of 119 $\mu$m is passed therethrough.

In order to detect the voids or contaminants located within material 12, overall system 10 includes an arrangement 18 for producing at its output a laser beam of electromagnetic radiation at a given wavelength, the beam being generally indicated at 20. This arrangement which will be discussed in more detail hereinafter, is specifically one capable of producing a far-infrared laser beam at a number of different wavelengths within the far-infrared spectrum, that is, between 70 micrometers and 2000 micrometers, and specifically one having a wavelength of approximately 119 micrometers. This particular type of laser beam is selected for a number of reasons. First, material such as these recited above including polyethylene is practically transparent to this radiation. Second, it provides for detecting very small defects such as microvoids.

In addition to the laser producing arrangement 18, system 10 includes an overall optical arrangement 22 which serves a number of purposes in the embodiment illustrated in FIG. 1. First, it utilizes a conventional wire-grid polarizer 23 for examining, and if necessary, correcting the polarization output beam 20 to insure proper polarization thereof. Second, this optical arrangement utilizing a beam splitter 24 or other such means redirects beam 20 from its output path indicated at 25 along a path indicated 26 which is incident to and at a predetermined orientation with material 12, specifically normal to surface 14a.

As illustrated in FIG. 1, it can be seen that the lateral extent of the overall beam along incident path 26 is substantially equal to and in alignment with the outermost extent of surface 14a comprising the front face of material 12. In this way, as will be seen below, electromagnetic radiation from beam 20 is directed into and through the entire vertical extent of material 12.

As stated previously, the electromagnetic radiation of beam 20 is directed into and through material 12 along incident path 26. In this regard, it is important to note that the radiation which passes through the material unobstructed by voids or foreign matter within the material does so along predictable beam refraction paths indicated generally by the arrows 34. These paths may be readily predicted by those with ordinary skill in the art because the index of refraction of material is known and the incident beam is sufficiently controlled for controlling its angle of entry (incident angle) within the material. It should be apparent that when the beam enters the material normal to front surface 14a it is not refracted and when it exits the material normal to back surface 14b it is not refracted. Hence, as illustrated in FIG. 1, the unobstructed radiation passes through material 12 in a straight line. Obviously, this would not be the case if beam entry or exit were not normal to surfaces 14a and 14b. Nevertheless, the refraction which would take place could be predicted based on the angles of incident and indices of refraction. On the other hand, the electromagnetic radiation which impinges on a foreign particle or void, for example void 36 illustrated in FIG. 1, as it passes through material 12 is scattered thereby along predictable scattering paths including paths different than the refraction paths 34. Two such paths are indicated at 38 and 40.

In order to monitor the presence or absence of a void 36 or a foreign particle, system 10 includes conventional devices 42 and 43 for detecting electromagnetic radiation at a wavelength identical to that of beam 20. These devices, which will be discussed in more detail hereinafter, are respectively positioned in alignment with scattering paths 38 and 40 as illustrated, for detecting that portion of the scattered electromagnetic radiation directed along these paths. Each detecting device may include a suitable lens 44 for aiding in capturing scattered radiation. So long as the amount of radiation which is scattered along paths 38 and 40 is significantly greater than the background radiation also passing along the same paths, detectors 42 and 43 can easily discriminate between the presence and absence of a void or foreign particle. Background radiation may be defined as that radiation of the same wavelength, i.e. radiation from beam 20 which is not scattered radiation from a void or foreign particle. This would include radiation passing through the material 12 unobstructed by voids or foreign particles as well as radiation which is reflected off of the outer surface of the material. As stated previously, the paths taken by the refracted radiation or, at least, substantially all of the refracted radiation are predictable and, hence, the scattering path 38 or 40 which is different than the refraction path can be readily selected. Moreover, as will be discussed below, these scattering paths can be selected so that they are different than any reflecting paths.

As just stated, in order to minimize background noise, each of the detection devices 42 and 43 must be located on a scattering path which is different than any of the refraction paths 34 and preferably different than the reflection paths defined by radiation from beam 20 reflecting off of material 12.

As will be discussed below, in order to further minimize background noise, the scattering paths selected in a preferred embodiment are not only different than the refraction paths and reflection paths but are specifically selected so as not to extend entirely within any plane which includes the incident path 26 of beam 20. In this way, the possibility of selecting a scattering path which coincides with an unpredicted refraction or reflection path is substantially minimized, if not eliminated.

From the foregoing, it should be obvious that there must be a sufficient number of scattering paths resulting from the impingement of radiation from beam 20 on a void or foreign particle in material 12 in order to select particular paths meeting the requirements discussed above. Ideally, if the impinged radiation is scattered isotropically, the appropriate scattering paths can be readily selected to minimize if not completely eliminate background noise of the type described. In this regard, scattering of light from spherical particles has been treated extensively in the past. Mathematical formulations for both the intensity and polarization of scattered electromagnetic radiation are available in the technical literature for a single spherical particle and also for groups of such particles. As a general rule, it has been found that spherical voids or foreign particles having an average size (average diameter) which is approximately equal to the wavelength of radiation impinging on its surface will scatter the radiation isotropically. For wavelengths of light much larger than the average diameter of the scattering particle ($D/\lambda < <1$) the intensity distribution is symmetrical about the plane through the center of the sphere at right angles to the direction of propagation of the incident light. As the radius of the sphere is increased, more light is scattered in the forward-direction than in the opposite direction. When the diameter of the sphere is very large compared to the wavelength ($D/\lambda > > 1$) most of the incident light is forward-scattered. In actual practice, the voids to be detected are not spherical but more or less elliptical in shape which slightly changes the character of the scattered field. Nevertheless, the fact that they are not perfectly spherical in shape will not significantly alter the predicted scattering patterns.

From the foregoing, it should be apparent that there is one possible limitation which results from relying on a scattering pattern which is isotropic or somewhat isotropic for selecting the appropriate scattering paths. Specifically, as stated, the voids or foreign particles to be detected must be matched with the wavelength of impinging radiation so that the two are substantially equal. However, there is another limitation relating to the penetrability of specific insulating materials by specific electromagnetic radiation. The materials of interest with respect to the present invention are polyethylene, PVC and the like which, are, as stated, practically transparent to far-infrared laser radiation. Accordingly, in accordance with the present invention, laser beam 20 is a far-infrared beam and material 12 is polyethylene, PVC or other such compatible material. This, of course, limits the size of voids or foreign particles which produce an isotropic or near isotropic pattern to a size approximately equal to the particular wavelength of far-infrared radiation impinging the particles. Actually, it has been found that for particular wavelengths $\lambda$ within this far-infrared spectrum, the size of voids or foreign particles which can be accureately detected lies within a range between $\lambda/6$ and $2\lambda$.

In view of the foregoing, it should be readily apparent that the particular voids or foreign particles to be detected produce a scattering pattern sufficiently extensive so that scattering paths meeting the requirements discussed previously can be readily selected. As illustrated in FIG. 1, the scattering path 40 is located in front of material 12, that is, in the backward direction with respect to the incident beam along path 26. This, of course, places detector 43 in front of the material, that is, in the backward direction with respect to the incident beam. As a result, this detector is clearly outside the path of refracted radiation (paths 34) and radiation which might be reflected off of material 12.

The only possible type of background radiation which might reach detector 43 would be radiation reflected towards the detector from radiation which might be scattered from a relatively rough outer surface of the material. With regard to this possiblity, the scattered background radiation resulting from the rough surface of the material may be readily measured by the RMS height of the surface. In the case of smooth material 12, it is anticipated that this height will be considerably less than the wavelength of impinging radiation and, hence, relatively smooth. Moreover, it can be assumed that the scattering from a relatively smooth surface is mostly specular in nature and hence passes behind the material, that is, in a forward direction with respect to the incident beam.

It is, however, desirable to utilize more than one detector and, in fact, it is desirable to locate a detector behind material 12, that is, in a forward direction with respect to the incident beam. Therefore, the scattering path selected, for example path 38, must be one which does not receive refracted background radiation or specular background radiation. As stated previously, this scattering path can be readily selected to be outside of the path of predicted refractive radiation as well as predicted reflected radiation. However, in order to minimize the possibility that scattering path 38 coincides with an unpredicted refraction path (or reflection path for that matter), path 38 is vertically inclined, that is, at an acute angle $\theta(v)$ vertically with the incident beam, as seen in FIG. 1, but more importantly it should be horizontally inclined, that is, at an acute angle $\theta(h)$ horizontally with the incident beam, as seen in FIG. 2. In other words, in the preferred embodiment of the present invention, scattering path 38 is selected so as not to extend entirely within any plane which includes the incident path of beam 20, that is, path 26. In this way, the possibility of refracted radiation or reflected radiation from detector 42 is minimized, if not eliminated, unless of course the radiation either impinges on a foreign particle or non-homogeneous section in material 12 or on an irregular surface thereon. Obviously, detector 43 can be located in the same vertically/horizontally inclined manner.

From the foregoing, it should be quite apparent that the scattering paths used for detecting scattered radiation from voids or foreign particles can be readily selected when the scattering pattern is isotropic or near isotropic. On the other hand, when the scattering pattern is more limiting, it becomes more difficult to select appropriate scattering paths. However, it is to be understood that the present invention is not limited to the detection of particular voids using a particular radiation beam which together provides isotropic or near isotropic scattering patterns. However, once the particular material 12 is selected and an electromagnetic radiation beam within a compatible sprctrum (between 70 microns and 2000 microns) is chosen, the scattering pattern of voids or foreign particles within a particular size range, within practical limits, can be readily determined. Once this pattern is determined and both the predicted refraction and reflection paths are plotted, scattering paths 38 and 40 as well as other scattering paths which meet the requirements discussed above can be readily selected. For example, based on actual scattering pattern in a working embodiment of the present invention, forward scattering path 38 was selected such that $\theta(V)$, that is, the vertical acute angle between the scattering path and incident path 26, is approximately equal to 0° and $\theta(h)$, that is, the horizontal acute angle, is approximately equal to 20°. It is to be understood, that $\theta(V)$ and $\theta(h)$ are not limited to these particular values.

The detectors themselves, like beam producing arrangement 18 may be conventional. Obviously, it will be necessary to select a device adapted to detect radiation at the wavelength of beam 20. In this regard, the size range of particles to be detected can be enlarged by generating a laser beam made up of a number of wavelengths, compatible, of course, with material 12 from both an index of refraction standpoint as well as absorption coefficient standpoint. Obviously, the detector then has to be selected to detect this multiwavelength radiation.

Once the detected radiation reaches a predetermined threshold level at a given detector, for example detector 42 (or 43), the latter will generate an output signal. The threshold level of detector 42 (or 43) is selected to indicate the presence of a void or foreign particle in the size range of interest and the signal at its output will represent such a void or foreign particle and may be used in a number of ways. For example, this output signal can be merely to drive visual or permanent readouts with or without an appropriate alarm. On the other hand, it could be used in an overall feedback arrangement not only for monitoring material 12 for voids and foreign particles, but also for regulating the process which produces the material for minimizing or eliminating these voids and contaminants.

In view of the foregoing, it should be readily apparent that system 10 is provided for detecting voids and/or foreign particles of particular sizes in plastic material, which material has a known index of refraction and an absorption coefficient sufficient to pass electromagnetic radiation of a given wavelength. As stated previously, this is accomplished by producing a far-infrared laser beam of electromagnetic radiation at a particular wavelength within the FIR spectrum and directing this beam into the material along a path incident to and at a predetermined orientation therewith. In this way, a portion of the beam which passes through the material unobstructed by voids or foreign matter therein does so along predictable beam refraction paths as does a portion which is reflected off of the outer surface of the plastic material. Moreover, any portion of the beam which impinges on one of the voids or foreign particles as it passes through the material is scattered thereby from predictable scattering paths including scattering paths different than the refraction paths or reflection paths. In this way, a suitable device for detecting FIR radiation at the particular wavelength may be positioned in alignment with one of these different scattering paths to provide indicative outputs for a void or foreign particle as discussed above.

Having described system 10 illustrated in FIGS. 1 and 2, attention is now directed to FIG. 3. This latter figure illustrates a far-infrared laser system used for detection of defects in plastics, specifically voids and foreign particles. A FIR laser generally indicated at 52 is optically pumped by a grating-tuned carbon dioxide ($CO_2$) laser 54 emitting in the 9.6 microns band. Within this band, there are a group of lines which can be selectively made to oscillate by an angular tuning of the grating inside the $CO_2$ laser cavity. The $CO_2$ laser line is selected to match within the linewidth of the absorbing gas which fills the FIR waveguide cavity. A finer tuning of the $CO_2$ laser line is accomplished by applying a dc voltage to the piezoelectric transducer (PZT) 56, such that the pump laser line is in coincidence with the absorbing line center. The output of the $CO_2$ laser is chopped mechanically by an arrangement generally indicated at 58 and at a frequency which is used as a reference signal to a lock-in amplifier 60. The $CO_2$ laser output is injected into the FIR laser cavity through an entrance at which the $CO_2$ laser beam is at its focal point. This optical alignment is accomplished by means of the mirror combination $M_1$ and $M_2$ as shown in FIG. 3.

The output of the FIR laser is focused onto the plastic sample 62 (corresponding to sample 12 in FIG. 1) in the form of a slab and normally to its front and back surfaces 64a and 64b. The primary beam in the forward direction, that is, the unobstructed beam indicated at 66, is collected by a calorimeter 68 and the scattered FIR radiation from defects is collected by a 4 inch aperture collecting lens 72 which is placed in front of a FIR photodetector (a gallium doped germanium crystal, submerging in liquid helium). This receiver system which consists of a detector and a collecting lens is looking at the sample and is oriented at a predetermined position so that the measured scattered laser power can be correlated to the size of the defect. More details concerning the defect can be learned by using more than one receiver which can be placed at difference angular orientation along a circumference of a circle with its center at the slab sample. In the absence of sample material, each receiving channel has its own characteristic background noise level, corresponding to that indicated in FIG. 4. In the presence of a plastic sample, a slight increase in the scattering level is anticipated due to a residual scattering of otherwise a perfect sample material. A substantial increase in the scattering level is expected if the sample contains a defect whose average size is approximately $\lambda/6$, where $\lambda$ is the laser wavelength. The scattered level increase rapidly with increasing defect size until the defect size reaches that of the focused laser beam.

What is claimed is:

1. A system for detecting the presence and character including size of one or more foreign particles or voids as small as one-sixth of a given wavelength in material of the type having characteristics including a known absorption coefficient and a known index of refraction such that said material is substantially transparent to radiation at said given wavelength and at said wavelength passes substantially all of said radiation therethrough except for some of the radiation impinging said particles or voids, said system comprising:

(a) means for producing a laser beam of electromagnetic radiation at said given wavelength, said given wavelength being within the far-infrared range of about 70 microns to about 2000 microns;

(b) means for directing said beam into said material along a path incident to and at a predetermined orientation with said material such that (i) any portion of said beam which passes through said material unobstructed by voids or foreign matter within said material does so along predictable non-impinging paths through said material and (ii) any portion of said beam which impinges one of said foreign particles or voids as it passes through said material is scattered thereby along predictable scattering paths different than said non-impinging paths; and (c) means for detecting electromagnetic radiation of said given wavelength, said means being positioned in alignment with at least one of said different scattering paths, whereby to detect any of said scatter electromagnetic radiation which is directed along said lastmentioned scattering path.

2. A system according to claim 1 wherein said wavelength is approximately 119 μm.

3. A system according to claim 1 wherein said material is polyethylene material.

4. A system according to claim 1 wherein the outer surface of said material is sufficiently smooth so to substantially eliminate any back scattering of electromagnetic radiation in front of said material and wherein said detecting means and its associated scattering path are located in front of said material at an acute angle with the incident path of said beam.

5. A system according to claim 1 wherein the outer surface of said material is sufficiently smooth so as to cause some of the electromagnetic radiation from said beam to be reflected off of said smooth surface along predictable paths passing beyond and behind said material and wherein said detecting means and its associated scattering path is located behind said material and out of any of said reflecting paths.

6. A system according to claim 1 wherein the foreign particles and voids to be detected are shaped and sized relative to said given wavelength such that said beam portion impinging on one of said particles or voids is scattered substantially isotropically.

7. A system according to claim 1 wherein said lastmentioned scattering path is located behind said material and is selected so as not to extend entirely within any plane which includes the incident path of said beam.

8. A system according to claim 1 wherein the average size of said particle to be detected is between about one-sixth said given wavelength and twice said given wavelength.

9. A system according to claim 1 wherein said detecting means includes means for producing an output signal when the amount of said scattered radiation detected reaches a predetermined threshold level at any given instant during operation of said system, whereby to indicate the presence of a void or foreign particle.

10. A system according to claim 1 including means located behind said material for capturing and absorbing at least a portion of said unobstructed beam portion.

11. A system according to claim 1 wherein at least one of said predictable scattering paths extends in the forward direction behind said material as a result of the differences in the refractive index between said material and the particle or void being detected, said detecting means being located in alignment with said one path.

12. A system according to claim 1 wherein said foreign particles or voids are of the type having a predetermined scattering pattern when impinged on by said laser beam and wherein said detecting means is pre-positioned in accordance with said pattern.

13. A method of detecting the presence and character including size of one or more foreign particles or voids as small as one-sixth of a given wavelength in plastic material of the type having characteristics including a known absorption coefficient and a known index of refraction such that said material is substantially transparent to radiation at said given wavelength and, at said wavelength, passes substantially all of said radiation therethrough except possibly for some of the radiation impinging said particles or voids, said method comprising:

(a) producing a laser beam of electromagnetic radiation at said given wavelength, said given wavelength being within the far infrared range of about 70 microns and 2000 microns;

(b) directing said beam into said material along a path incident to and at a predetermined orientation with said material such that (i) any portion of said beam which passes through said material unobstructed by voids or foreign matter within said material does so along predictable non-impinging paths, and (ii) any portion of said beam which impinges one of said foreign particles or voids as it passes through said material is scattered thereby along predictable scattering paths including paths different than said non-impinging paths; and (c) detecting the scattered electromagnetic radiation of said given wavelength which is directed along one of said different scattering paths.

14. A method according to claim 13 wherein at least one of said predictable scattering paths extends in the forward direction behind said material as a result of the differences in the refractive index between said material and the particle or void being detected, said scattered radiation being detected along said one path.

15. A method according to claim 13 wherein said foreign particles or voids are of the type having a predetermined scattering pattern when impinged on by said laser beam, said method including the steps of predetermining said pattern to predict said different scattering paths and positioning a radiation detector on one of said last-mentioned paths in based said pattern.

* * * * *